(12) United States Patent
Enerson et al.

(10) Patent No.: US 7,641,174 B2
(45) Date of Patent: *Jan. 5, 2010

(54) DOME CHECK VALVE (75) Inventors: Jon R. Enerson, Port Richey, FL (US); Pavel T. Miller, St. Petersburg, FL (US); Gregory S. Jordan, Palm Harbor, FL (US)

(73) Assignee: Halkey-Roberts Corporation, St. Petersburg, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/942,002

(22) Filed: Nov. 19, 2007

(65) Prior Publication Data
US 2008/0087859 A1 Apr. 17, 2008

Related U.S. Application Data (63) Continuation of application No. 11/238,680, filed on Sep. 29, 2005, now Pat. No. 7,296,782.

(60) Provisional application No. 60/615,479, filed on Oct. 1, 2004.

(51) Int. Cl.
- F16K 51/00 (2006.01)
- F16L 29/00 (2006.01)
- F16L 37/28 (2006.01)

(52) U.S. Cl. ............. 251/149.6; 137/859; 604/249; 604/256

(58) Field of Classification Search ............ 251/149.1, 251/149.6, 149.7; 137/859; 604/249, 256
See application file for complete search history.

(56) References Cited

U.S. PATENT DOCUMENTS

| | | | |
|---|---|---|---|
| 3,831,629 A | 8/1974 | Mackal et al. | |
| 4,369,812 A | 1/1983 | Paradis et al. | |
| 4,434,965 A | 3/1984 | St. Martin, Jr. | |
| 4,499,916 A | 2/1985 | Hanson et al. | |
| 4,744,391 A | 5/1988 | Lardner | |
| 4,998,562 A | 3/1991 | Foltz | |
| 5,349,984 A | 9/1994 | Weinheimer et al. | |
| 5,395,348 A * | 3/1995 | Ryan | 604/247 |
| 5,409,042 A | 4/1995 | Kirchner | |
| 5,465,938 A | 11/1995 | Werge et al. | |
| 5,529,278 A | 6/1996 | Weldon et al. | |
| 5,573,516 A | 11/1996 | Tyner | |
| 5,634,491 A | 6/1997 | Benedict | |
| 5,746,414 A | 5/1998 | Weldon et al. | |
| 5,855,355 A | 1/1999 | Grunert et al. | |
| 5,904,334 A | 5/1999 | Grunert et al. | |

(Continued)

OTHER PUBLICATIONS

PCT Int. Prel. Report, May 21, 2007 (US2005/035205).

*Primary Examiner*—John K Fristoe, Jr.
(74) *Attorney, Agent, or Firm*—Gray Robinson, P.A.

(57) ABSTRACT

A valve comprising an inlet housing, an outlet housing, an elastomeric valve element having a generally dome-shaped configuration with a central integral stem positioned substantially concentrically therewith, the inlet housing and outlet housing being fastened together at a joint with the elastomeric valve element positioned therein and the valve element including a plurality of longitudinal ribs formed along an outer annular periphery of a lower end of the dome-shaped configuration that define flow channels that allow fluid flow from across an upper surface of the dome-shaped configuration through the flow channels.

14 Claims, 11 Drawing Sheets

U.S. PATENT DOCUMENTS

| | | |
|---|---|---|
| 5,992,462 A | 11/1999 | Atkinson et al. |
| 6,311,712 B1 | 11/2001 | Meyer |
| 6,390,120 B1 | 5/2002 | Guala |
| 6,397,884 B1 | 6/2002 | Miyajima et al. |
| 7,296,782 B2 | 11/2007 | Enerson et al. |

* cited by examiner

DOME CHECK VALVE

CROSS-REFERENCE TO RELATED APPLICATIONS

This application is a continuation patent application of U.S. patent application Ser. No. 11/238,680 filed Sep. 29, 2005, now U.S. Pat. No. 7,296,782, which claims the benefit of provisional application No. 60/615,479, filed Oct. 1, 2004, the disclosures of each of which are hereby incorporated by reference herein.

BACKGROUND OF THE INVENTION

1. Field of the Invention

This invention relates to check valves, and relates more specifically to a check valve for needleless medical usage.

2. Description of the Background Art

Presently, there are many types of check valves which are designed to control the one-way flow of a fluid therethrough. One common type of check valve comprises a valve element, such as a ball or spring biased valve stem, reciprocatingly positioned within a valve body providing a fluid passageway. The flow of fluid in one direction through the valve body is permitted upon displacement of the stem as it flows around the valve stem to exit the valve body. In the opposite direction, however, the fluid pressure along with the spring forces the valve stem against a valve seat, thereby inhibiting, or checking the flow of fluid therethrough. In this manner, this type of check valve effectively provides that fluid can flow only in one direction through the check valve. An example of this type of valve is found in U.S. Pat. No. 5,349,984, the disclosure of which is incorporated by reference herein.

Check valves employing an elastomeric stem without the use of a spring are described in U.S. Pat. No. 3,831,629, the disclosure of which is incorporated by reference herein. Other check valves employing umbrella or disk-like elastomeric elements are described in the following U.S. Pat. Nos. 5,992, 462; 4,499,916 and 4,369,812, the disclosures of which are incorporated by reference herein. Some check valves employ elastically deformable diaphragm-like elements as described in U.S. Pat. No. 6,390,120, the disclosure of which is incorporated by reference herein. Another check valve employing conical or hollow elastomeric elements where fluid flow is arranged to pass through the element itself is described in U.S. Pat. Nos. 5,573,516 and 5,746,414, the disclosures of which are incorporated by reference herein. Some of the designs described above allow for bi-directional fluid flow if accessed by the appropriate connector such as a luer fitting commonly used in the medical fluid delivery field.

There is a need in the industry to provide a reliable and economical check valve providing a reliable seal when checked by very low back pressures such as low fractions of pounds per square inch (PSI) while sealing at high back pressures, preferably in the range of 10-100 PSI. There is also a need for check valves that allow for an economical way to accommodate various preset opening or cracking pressure conditions. Most prior art valves of this nature employ springs that have varying spring properties, resulting in a check valve that provides different opening pressures without any component change.

More particularly, current pressure relief valves employ metal springs for accurate opening pressure settings. The presence of metal in an I.V. line presents possible contamination dangers from corrosion or metallic particles. Elimination of metal springs is therefore highly desirable. Check valves equipped with non-metal resilient sealing elements are designed for a specific opening pressure. The variability of this valve characteristic is therefore not easily achieved.

Most valves that are designed to seal at low pressures, such as disc valves, do not normally allow for high flow or bi-directional flow. Therefore, there exists a need in the industry to provide a check valve that accommodates relatively high fluid flow when unchecked.

Further, some valves with elastomeric elements where fluid flow is arranged to pass through the element itself have a possibility of particulate contamination. Molding of small check valve elastomeric components commonly include small openings for fluid to pass through. Such openings are created by cores of very small dimensions. These core features could be relatively easily damaged and could therefore cause flash and result in small particles of flash potentially breaking off and contaminating the fluid flow.

Therefore, it is an object of this invention to provide an improvement which overcomes the aforementioned inadequacies of the prior art devices and provides an improvement which is a significant contribution to the advancement of the check valve art.

Another object of this invention is to provide a check valve employing an elastomeric valve element that is economical to manufacture and assemble to achieve valves with different possible cracking pressure.

Another object of this invention is to provide a check valve that allows bi-directional high fluid flow when cracked.

Another object of this invention is to provide a check valve that maintains a seal when checked even at very low back pressures.

Another object of this invention is to provide a check valve that maintains a seal when checked even at high back pressures.

The foregoing has outlined some of the pertinent objects of the invention. These objects should be construed to be merely illustrative of some of the more prominent features and applications of the intended invention. Many other beneficial results can be attained by applying the disclosed invention in a different manner or modifying the invention within the scope of the disclosure. Accordingly, other objects and a fuller understanding of the invention may be had by referring to the summary of the invention and the detailed description of the preferred embodiment in addition to the scope of the invention defined by the claims taken in conjunction with the accompanying drawings.

SUMMARY OF THE INVENTION

For the purpose of summarizing the invention, this invention comprises a valve that seals itself to restrict fluid flow at very low back pressure. The valve element is made from an elastomeric material which is deflected after the line pressure reaches a predetermined level thus allowing flow in one direction and occluding the line in the opposite direction.

The hemispherical dome-like shaped elastomeric valve element is constructed in such a way to be deflectable, such as being activated by the external device such as a male luer, whereupon the valve then becomes a two-way valve allowing flow in both directions. The valve element is self-aligning by the valve seat geometry complementing valve element tapered seat features. The valve element is designed in such a way that various opening pressures are achievable by a simple modification of a mold tool, for example by changing a core pin.

The valve element of the valve is self-supporting and when assembled in the valve, exerts a predetermined pressure against the valve seat thus sealing the valve. The element deflects at the center after pressure rises over the predetermined cracking pressure thus opening the flow path. The element deflection is directed by a concentric groove or grooves positioned on the inside of the element dome area. The dimensions of the groove(s) determine the valve opening pressure. The simple variation of groove dimensions thus achieves the goal of providing an economical way for valves to be manufactured at various preset cracking pressure conditions.

The valve element positioned in the housing incorporates a set of ribs that allow high, unobstructed fluid flow. The valve element has no openings for fluid flow; instead the fluid flow is directed outside the valve element.

The valve has a relatively low, predetermined opening pressure one way and withstands relatively high back pressure in the opposite direction. Moreover, the valve housing is manufactured in a modular fashion, allowing the assembly of the same stem element into various housings having different connecting arrangements, such as ML, MLL, tubing fitment or barbed connector. The components of the envisioned new valve are producible reliably by high cavitation molds and are suitable for high speed assembly process, thereby resulting in a highly economical valve. None of the valve components require registration radially during assembly.

The foregoing has outlined rather broadly the more pertinent and important features of the present invention in order that the detailed description of the invention that follows may be better understood so that the present contribution to the art can be more fully appreciated. Additional features of the invention will be described hereinafter which form the subject of the claims of the invention. It should be appreciated by those skilled in the art that the conception and the specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

For a fuller understanding of the nature and objects of the invention, reference should be had to the following detailed description taken in connection with the accompanying drawings in which.

Similar reference characters refer to similar parts throughout the several views of the drawings.

DETAILED DESCRIPTION OF THE PREFERRED EMBODIMENTS

Figure 1:
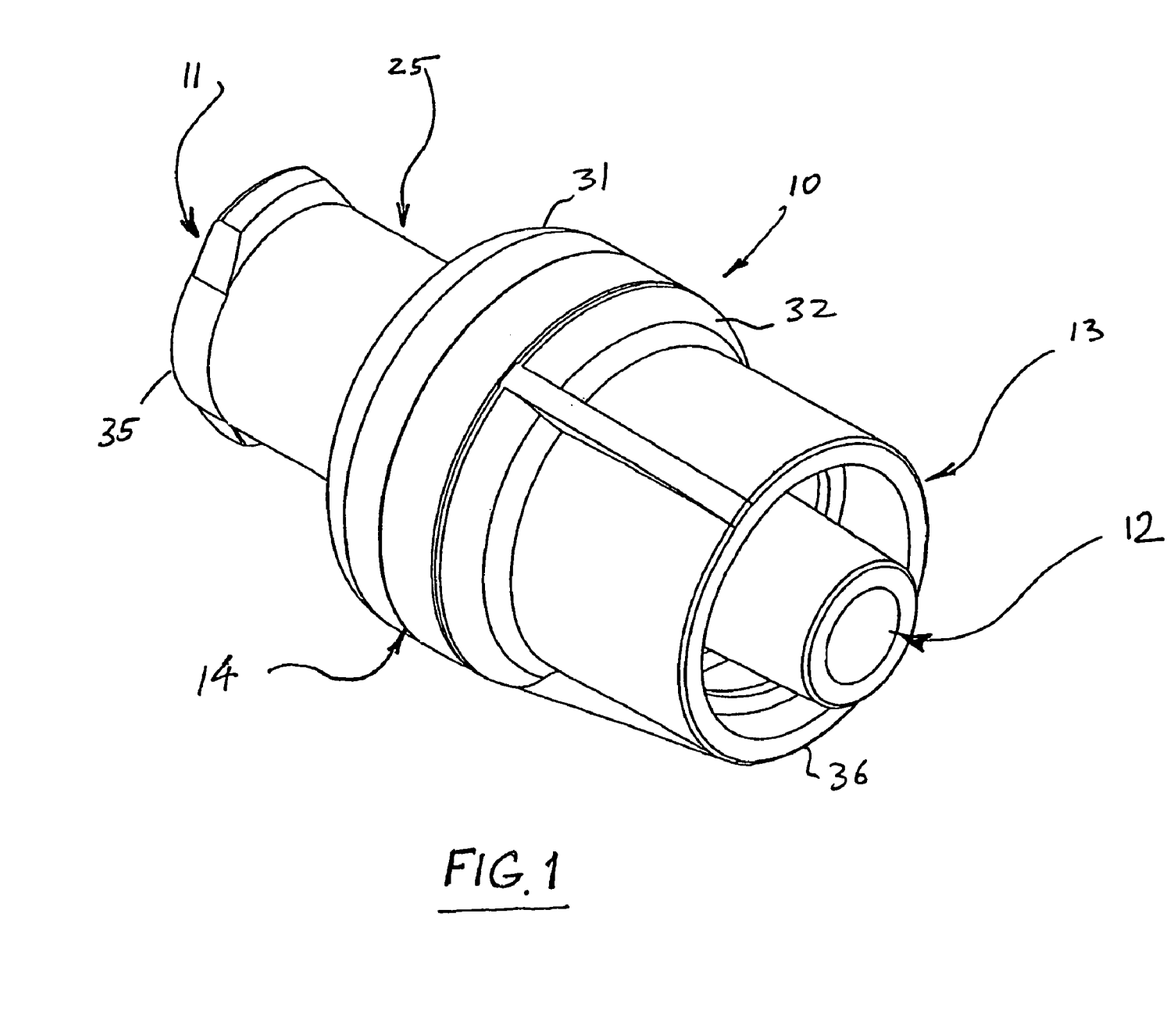
FIG. 1 is an enlarged isometric view of the valve of the invention having MLL inlet and outlet arrangement.
Figure 8:
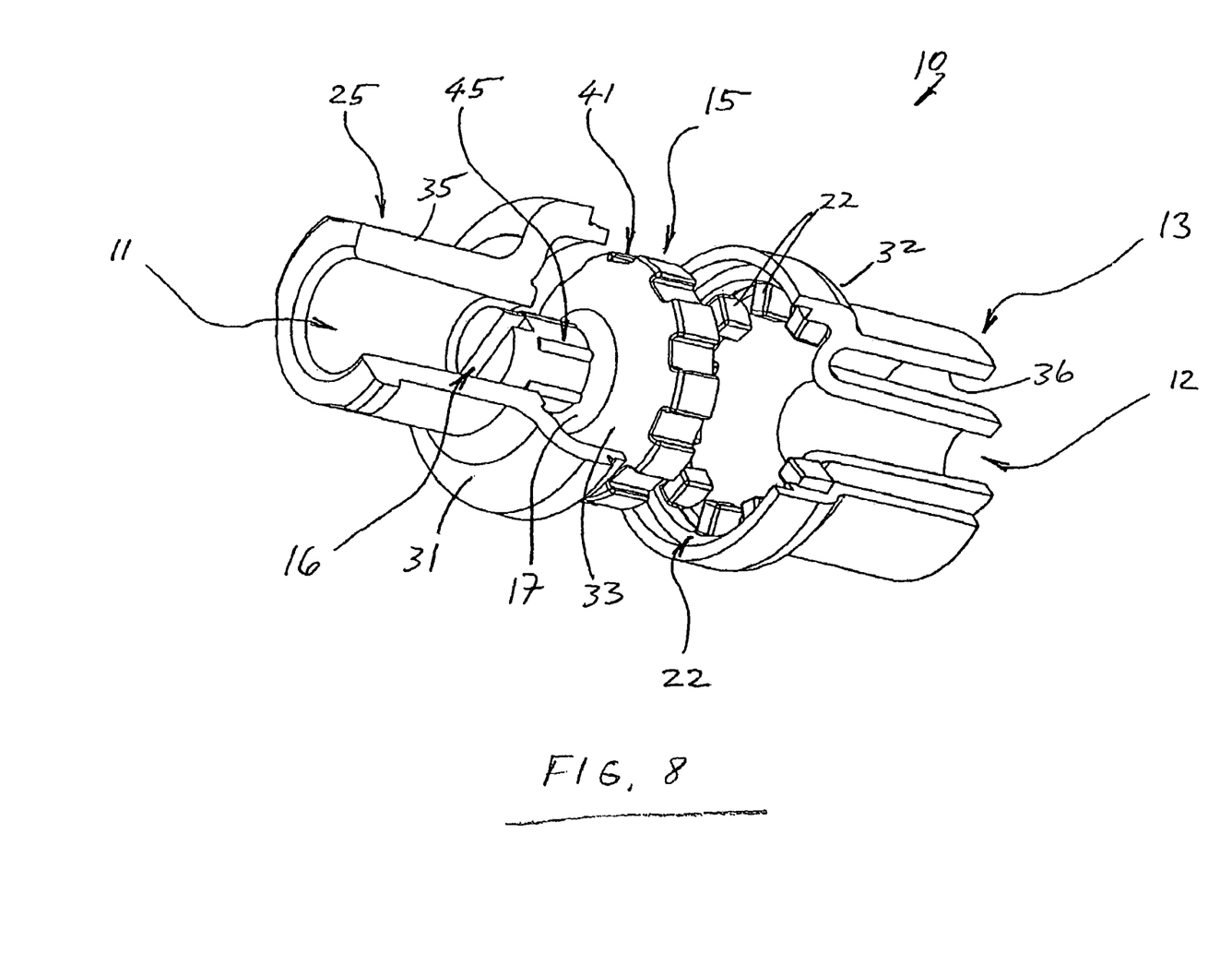
FIG. 8 is an isometric exploded view, partially in section, of the valve according to FIG. 1.
Figure 9A:
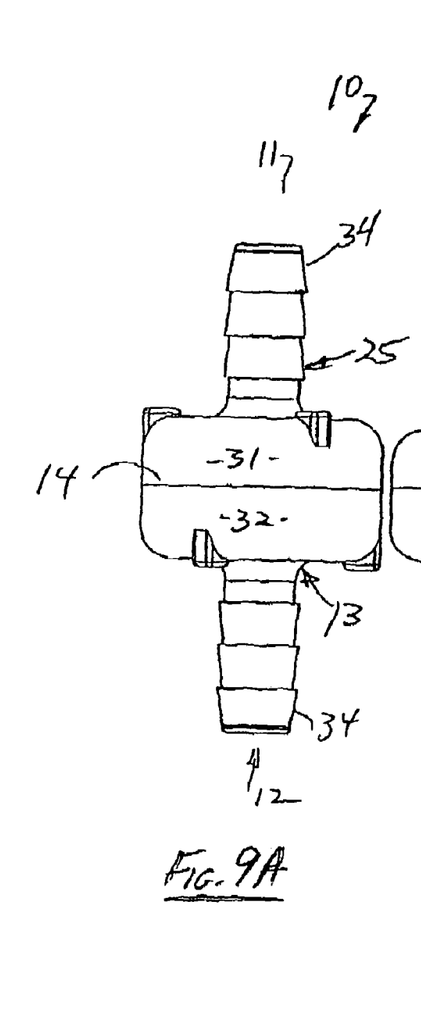
FIGS. 9A, 9B, 9C and 9D are side elevational views illustrating various fitting locations.
Figures 9B, 9C, 9D:
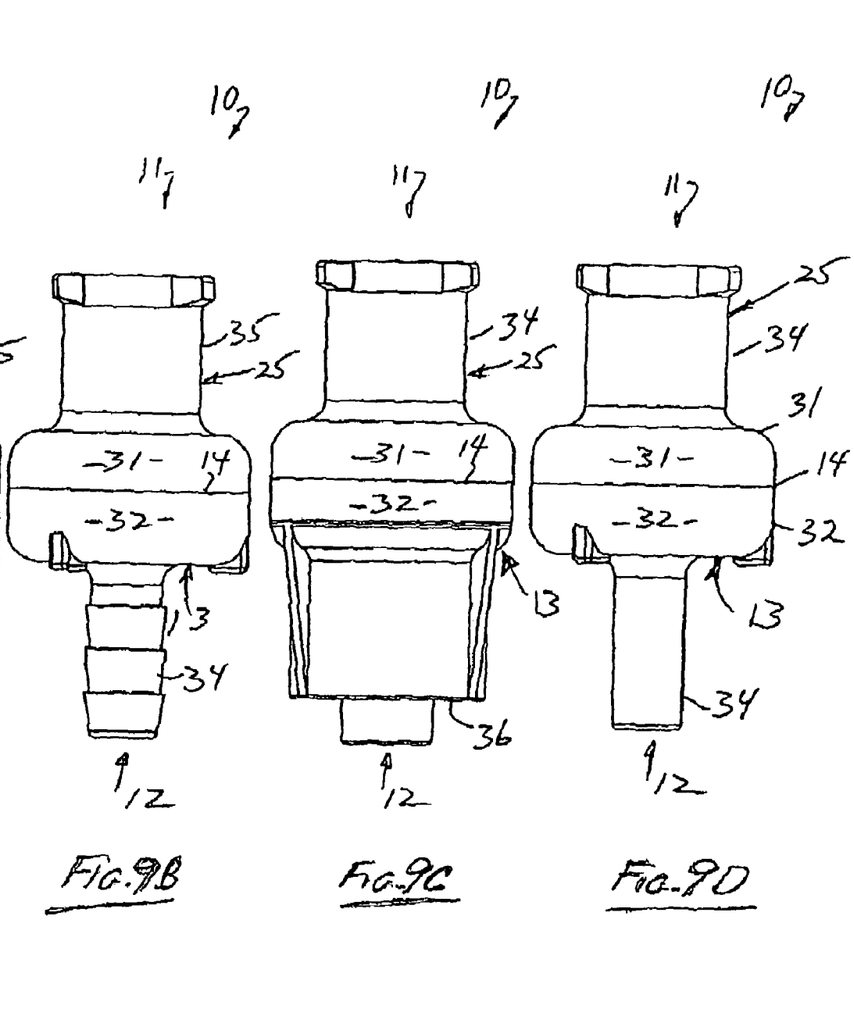

As best shown in FIGS. 1 and 8, the valve 10 of the invention comprises inlet housing 25 and an outlet housing 13 and an elastomeric valve element or stem 15. Housings 25 and 13 are permanently fastened together at joint 14 such as by welding or bonding.

Figure 2A:
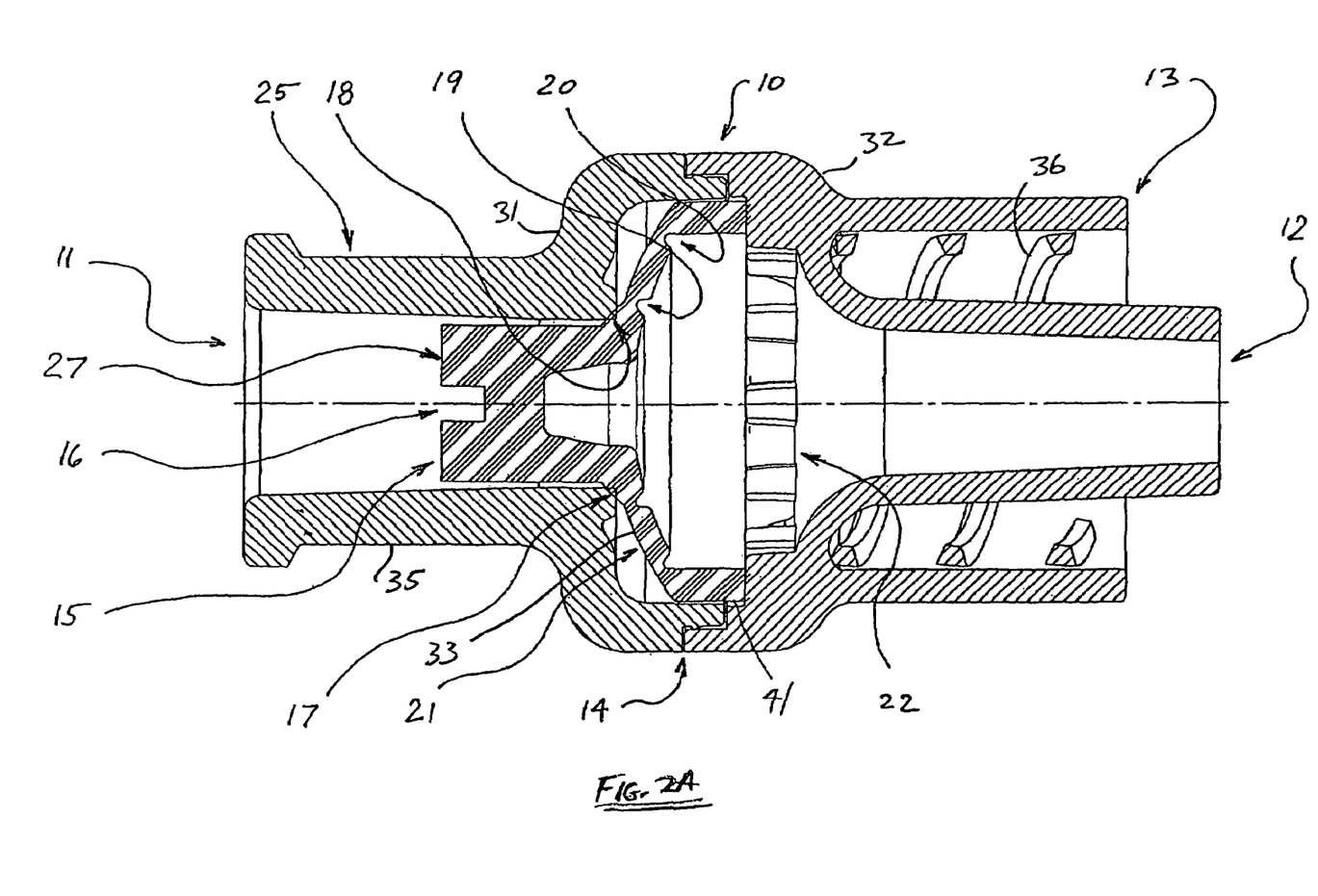
FIG. 2 is an enlarged cross-sectional view of the valve according to FIG. 1 showing the first embodiment of the valve element at rest stage.
Figure 2B:
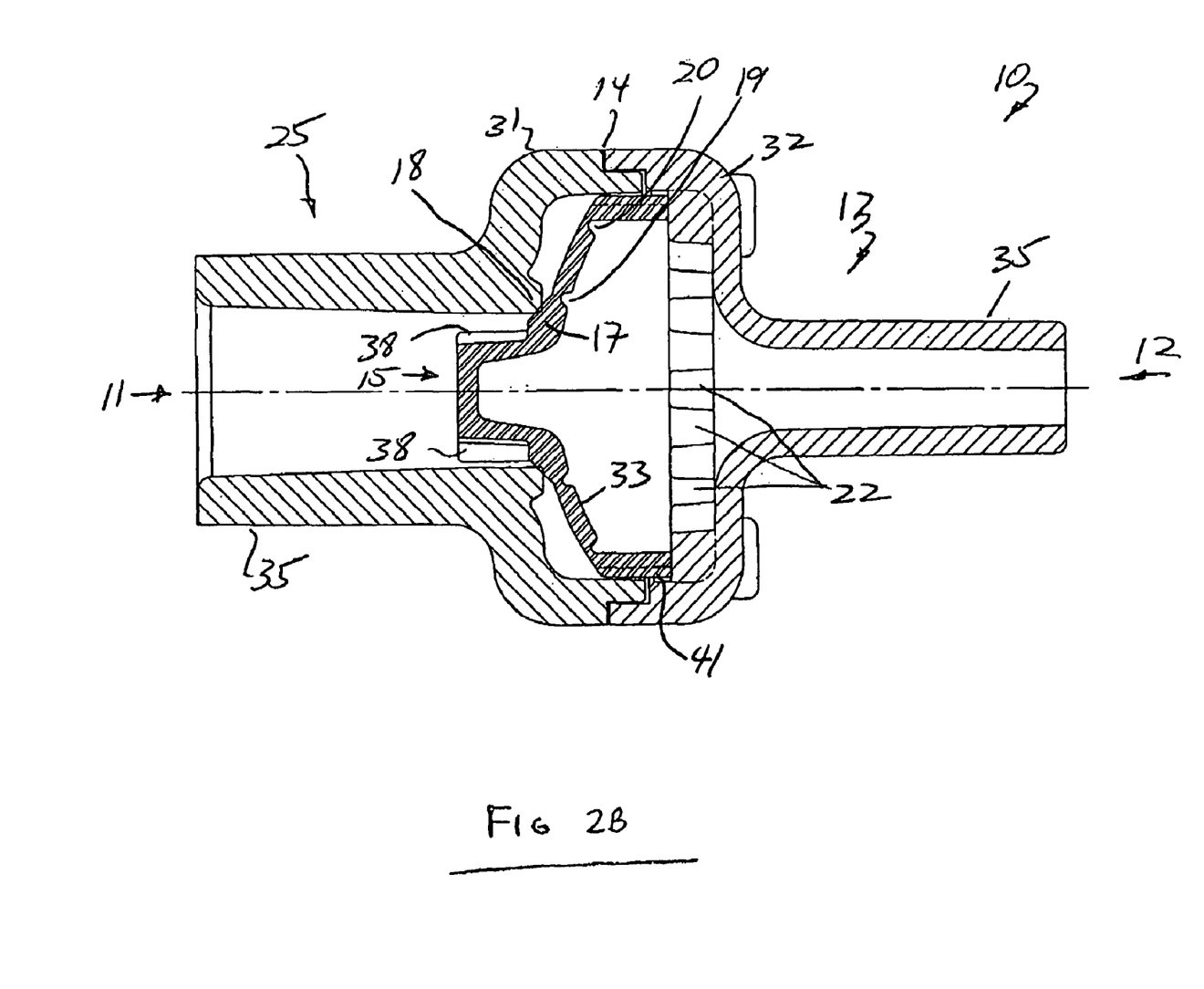

Referring to FIGS. 2A and 2B, the inlet housing 25 comprises a generally tubular configuration having a luer fitting 35 at its inlet 11 and a generally dome-shaped, larger diameter configuration 31 at its opposite end. Similarly, outlet housing 13 comprises a generally tubular configuration having a luer fitting 35 at its outlet 12 and a generally dome-shaped larger diameter configuration 32 at its opposite end which assembles with the dome-shaped end 31 of the inlet housing 25 at joint 14.

The inlet and outlet housings 25 and 13 may be provided with many types of fittings such as, in FIG. 8A, dual inlet and outlet barbed hose fittings 34, in FIG. 8B, inlet luer 35 and outlet hose barb fittings 34 (or vice versa), in FIG. 8C, inlet luer fitting 35 and outlet locking luer fitting 36 (or vice versa) and in FIG. 8D, inlet luer fitting 35 and outlet luer fitting 35 (or vice versa).

As shown in FIGS. 4A and 4B, 5A and 5B and 6, the valve element 15 comprises a generally dome-shaped configuration 33 with a central integral stem 42 positioned concentrically therewith.

Figure 4A:
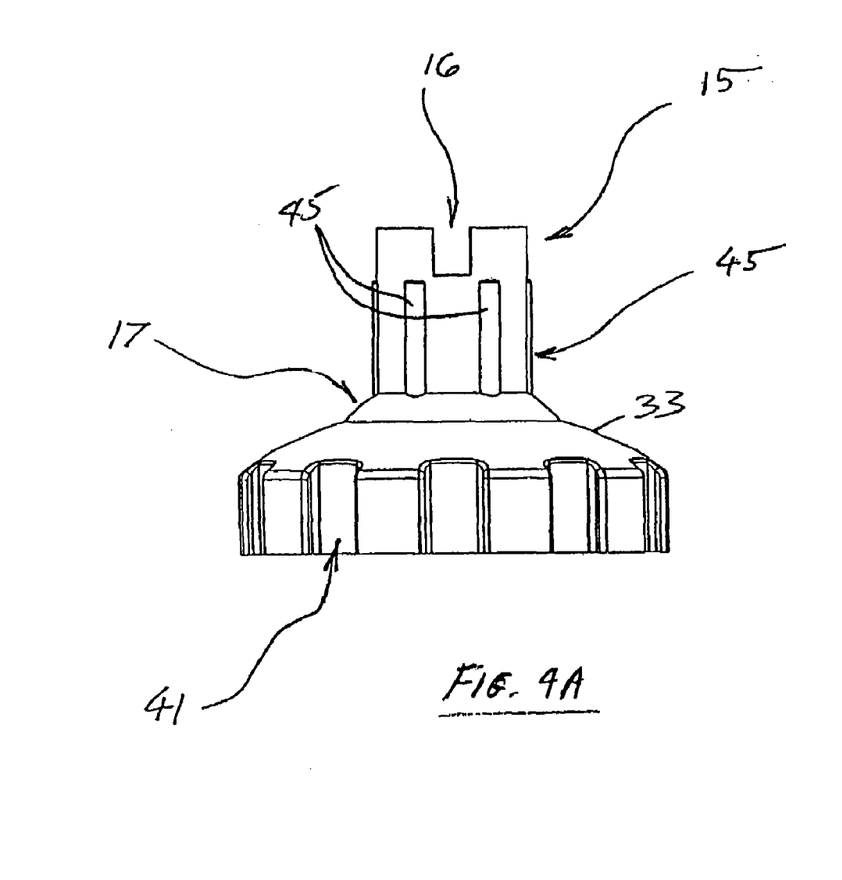
FIGS. 4A and 4B are side and isometric views of the first embodiment of the valve element with a ribbed stem.
Figure 4B:
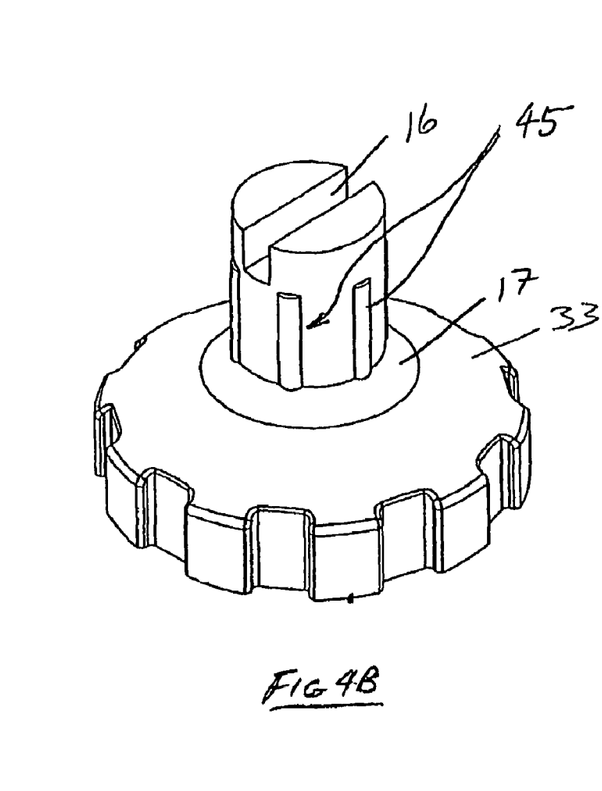
Figure 5A:
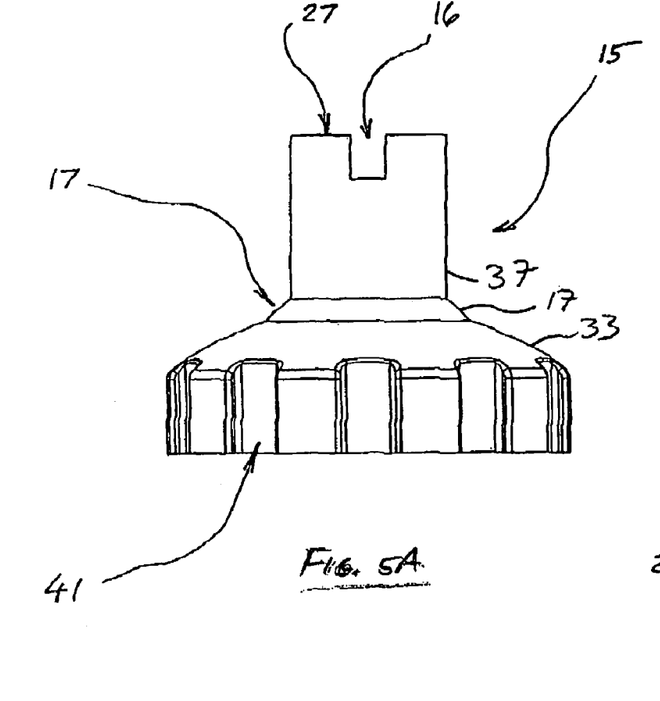
FIGS. 5A and 5B are side and isometric views of the second embodiment of the valve element with a smooth stem without inlet ribs.
Figure 5B:
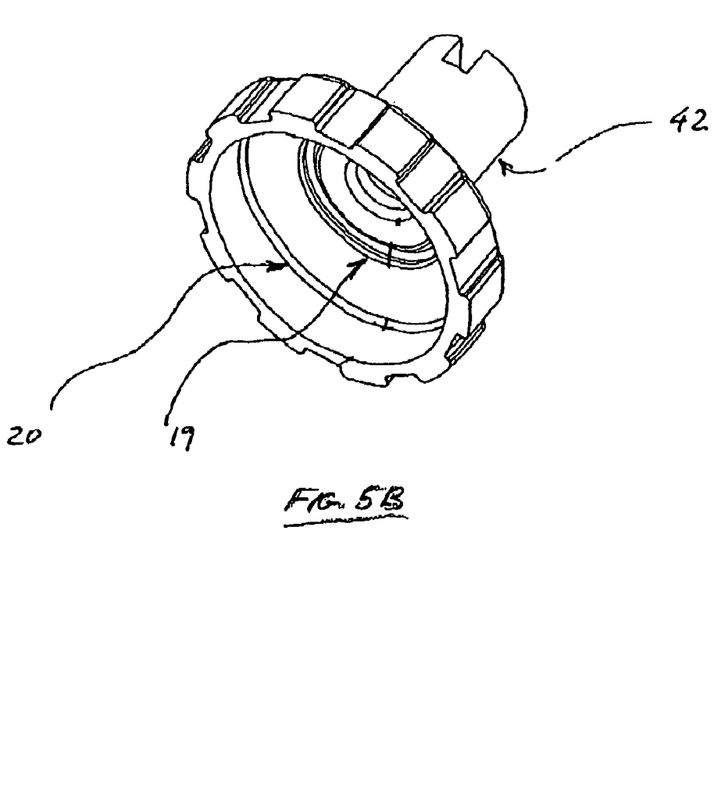
Figure 6:
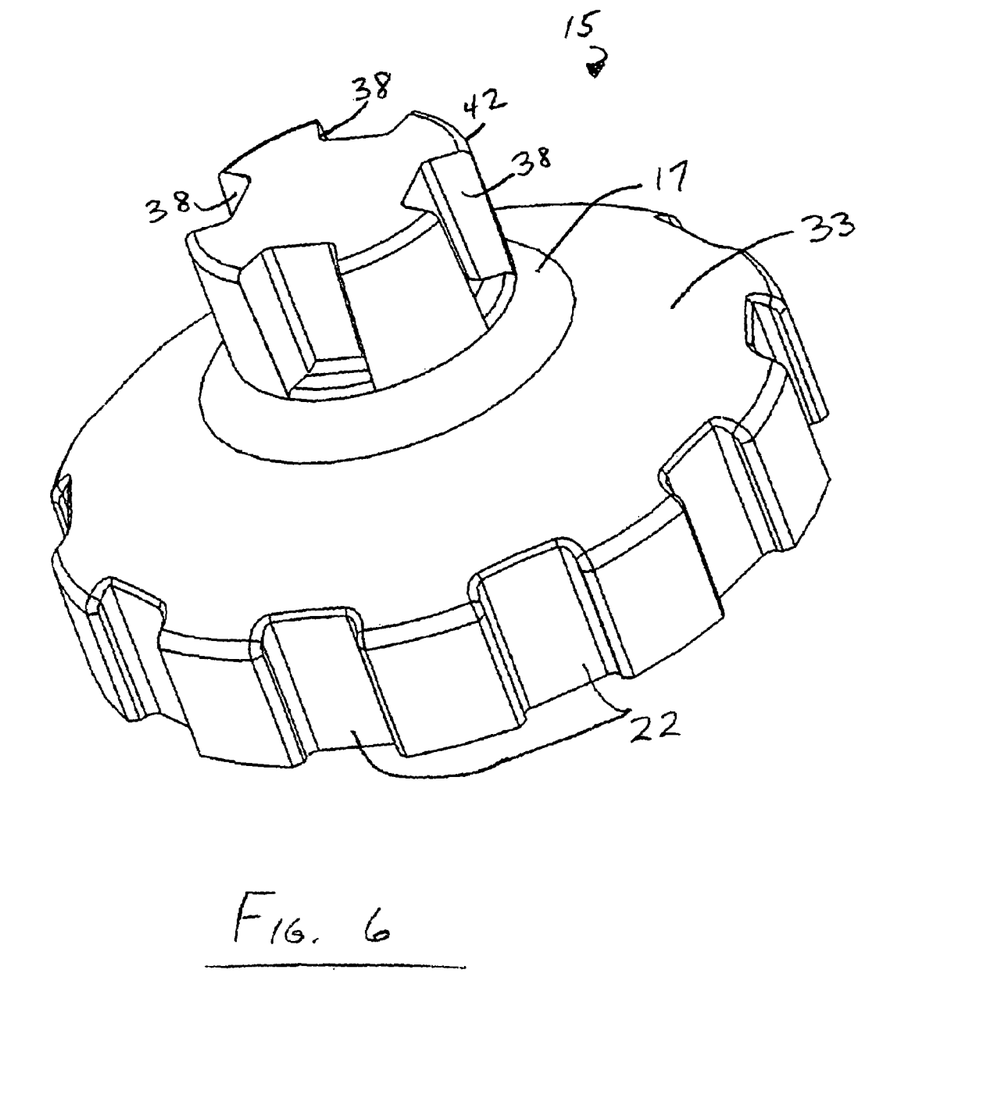
FIG. 6 is an enlarged isometric view of the third embodiment of the valve element with a notched stem.
Figure 7A:
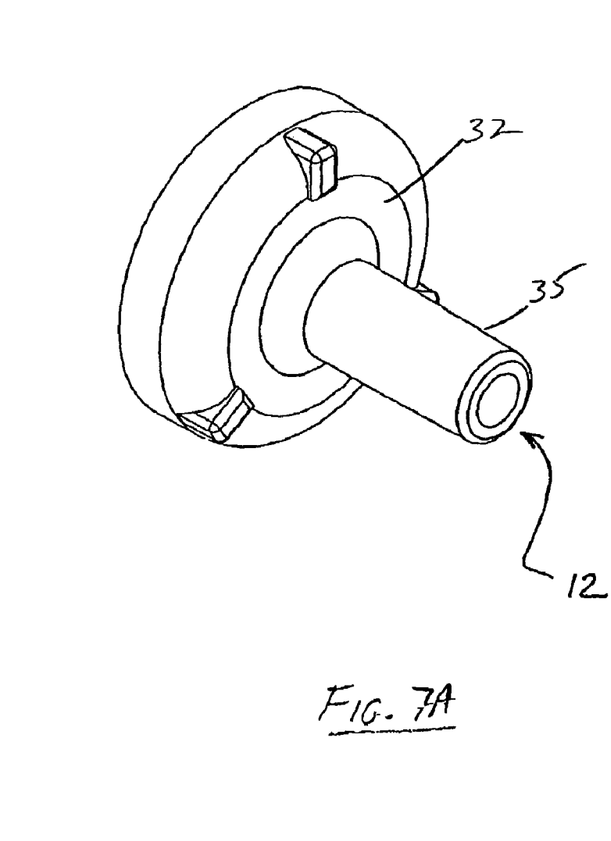
FIGS. 7A and 7B are enlarged isometric views of the outlet housing of the valve having a tubing connection arrangement.
Figure 7B:
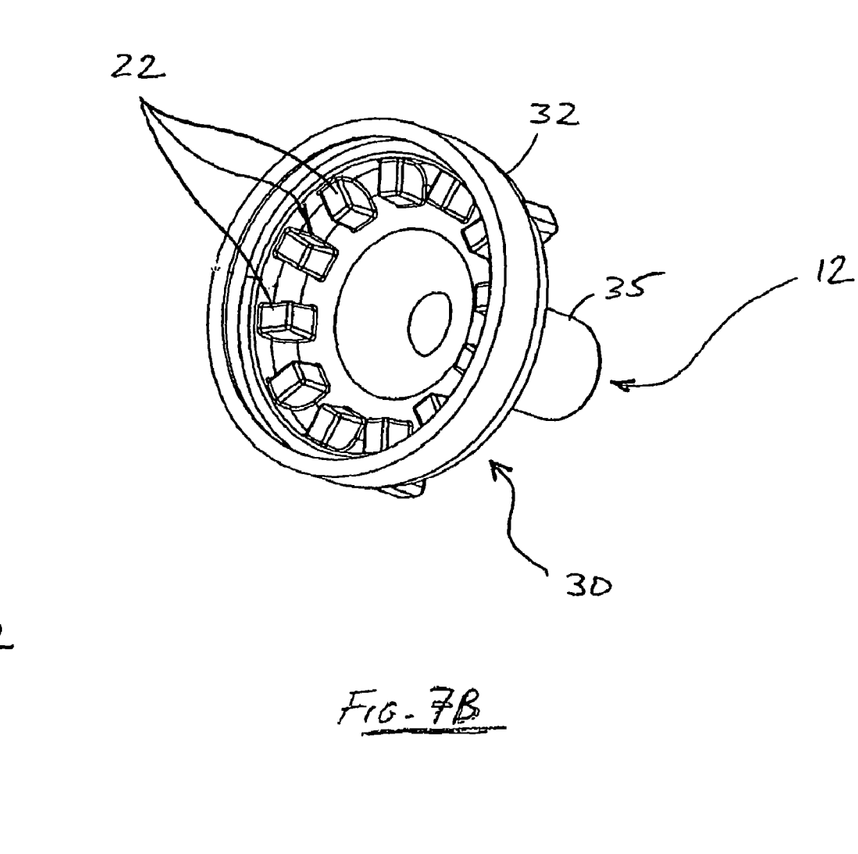

As shown in FIGS. 4A and 4B, in a first embodiment of the valve element 15, a plurality of ribs 45 may be positioned longitudinally along the length of the stem 42. Alternatively, as shown in FIGS. 5A and 5B, in a second embodiment of the valve element 15, the outer surface of the stem 42 may comprise a smooth cylindrical configuration 37. A stem slot 16 may be provided diametrically in the end of the stem 42 to allow fluid flow therethrough in the event the stem 42 is engaged by the tip of a luer fitting, syringe, or other device that might otherwise form a seal therewith. As shown in FIG. 6, in a third embodiment of the valve element 15, a plurality of notches 38 may be positioned longitudinally along the length of the stem 42.

The notches 38 preferably comprise a larger width toward the inlet 11 and a smaller width toward the dome-shaped configuration 33, and a depth radially inward to define a castellated configuration in the end of the stem 42 (as viewed axially). The depth of the notches 38 is sufficient to eliminate the need for the stem slot 16 since fluid may flow within channels formed by the notches 38 when the tip of luer fitting engages the end of the stem 42 without blockage as might otherwise occur without the stem slot 16 or the notches 38.

The valve element 15 further includes a plurality of longitudinal ribs 41 formed along the outer annular periphery of the lower end of the dome-shaped portion 33 of the valve element 15. The ribs 41 define flow channels that allow fluid flow from across the upper surface of the dome-shaped configuration 33 through the flow channels. Viewing FIGS. 4A and 4B, 5A and 5B and 6 in conjunction with FIGS. 7A and 7B and 8A and 8B, it is seen that the outlet housing 13 correspondingly includes a plurality of castellations 22 formed along the inner annular periphery of the dome-shaped portion 32 of the outlet housing 13 to define flow channels. Referring also to FIGS. 2A and 2B, the lower edge of the dome-shaped portion 33 of the valve element 15 is juxtapositioned against the upper surfaces of the castellations 22 when the valve 10 is assembled. Preferably, the relative annular spacing and size of the castellations 22 is different from the annular spacing and size of the ribs 41 such that no blocking occurs and fluid flow is allowed through the flow channels defined by the ribs 41 and the flow channels defined by the castellations 22 from the inlet 11 to the outlet 12 of the valve 10. Specifically, the ribs 41 and the castellations 22 may be configured differently, such as being odd or even in number, staggered, or positioned asymmetrical, such that they are not allowed to fit into each other and otherwise restrict the fluid flow therethrough.

Figure 3A:
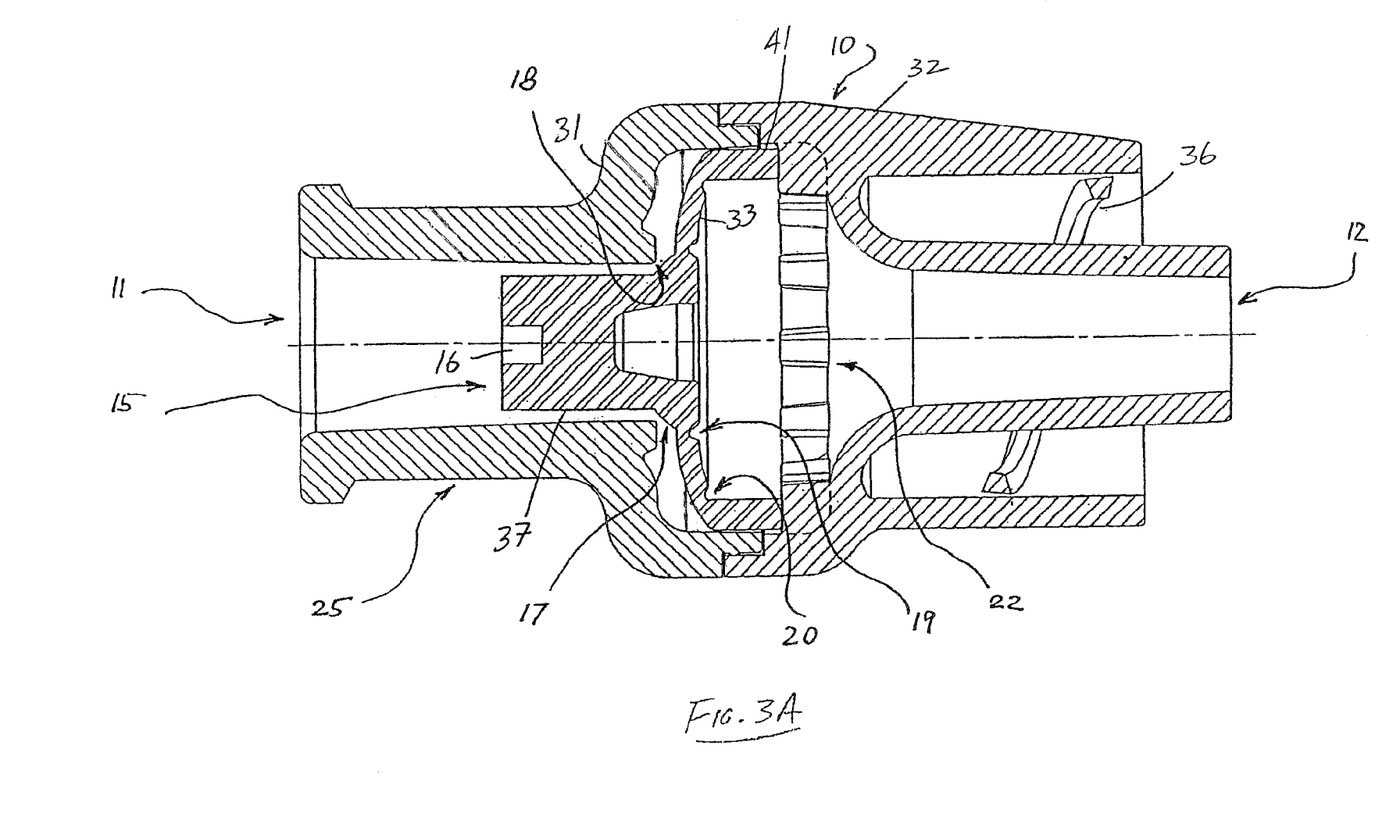
FIG. 3 is an enlarged cross-sectional view of the valve according to FIG. 1 showing the first embodiment of the valve element at open stage.
Figure 3B:
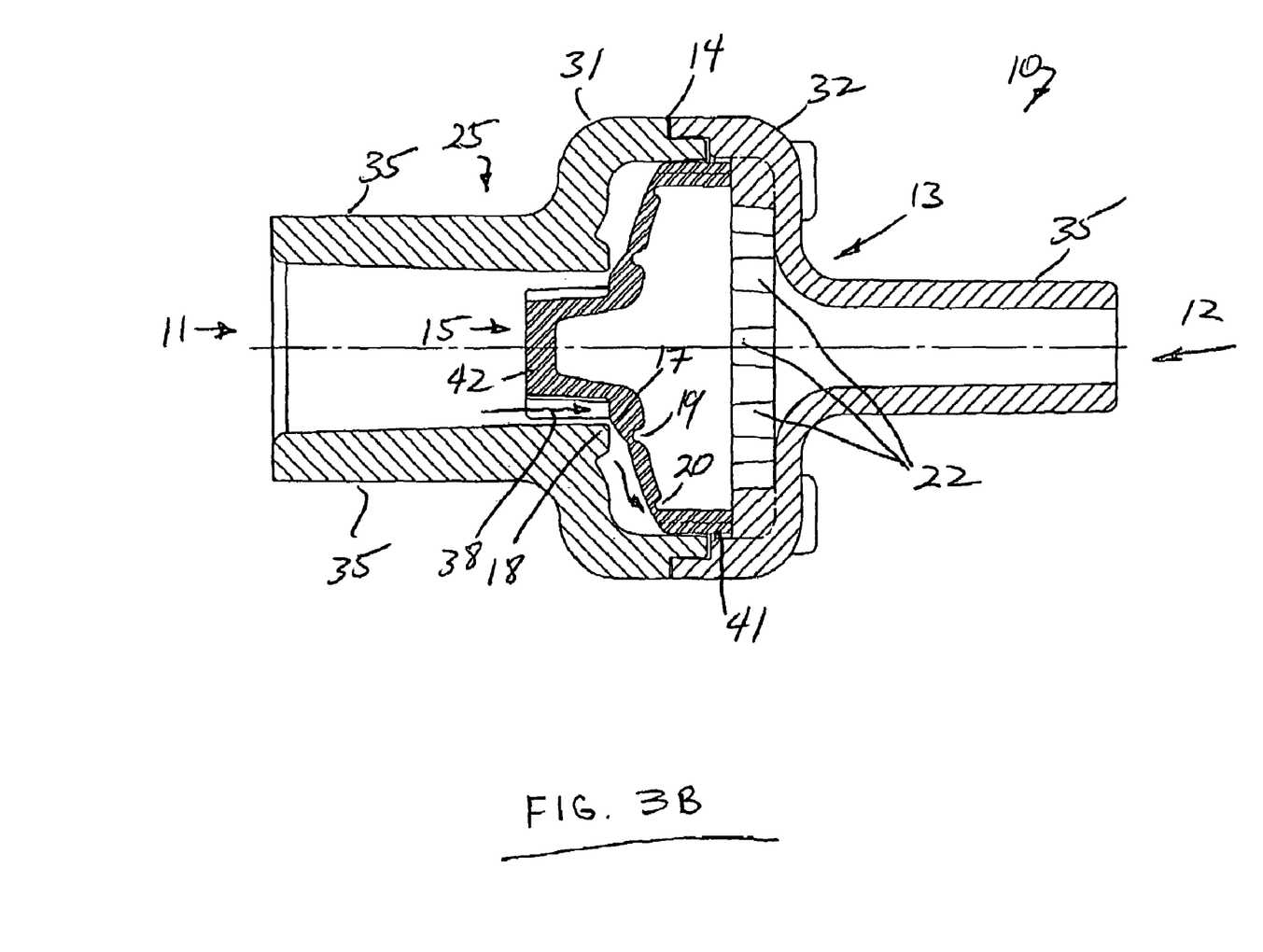

As best shown in FIGS. 2A and 2B, 3A and 3B and 4A and 4B, the valve element 15 further comprises one or more annular reliefs 19 and 20 formed concentrically in the underside or upper surface of the dome-shaped portion 33 of the valve element 15. The reliefs 19 and 20 may each comprise a continuous groove, a series of indentations aligned annularly, or other continuous or intermittent arrangement of reliefs 19 and 20 that allow easier flexing, similar in function to a living hinge, when the valve element 15 is forced to its cracked or opened position (FIGS. 3A and 3B). The number and dimensions of the reliefs 19 and 20, together with the elastomeric properties of the valve element 15, define the cracking pressure necessary to crack or open the valve element 15.

More particularly, the upper portion of the dome shape configuration 33 of the valve element 15 comprises a generally frustro-conical neck 17 that is in alignment with an annular valve seat 18 to form a fluid-tight annular seal therewith by virtue of the resiliency of the valve element 15 pushing its frustro-conical neck 17 into sealing engagement with the valve seat 18. It should be appreciated that valve elements 15 of different elastomeric properties and/or reliefs 19 and 20 of different dimensions and/or different number of reliefs 19 and 20, could easily be manufactured and assembled with the valve housings 25 and 13 to thereby produce valves 10 having different cracking pressures.

In operation, fluid flow through the housing outlet 12 is blocked by virtue of the frustro-conical neck 17 being resiliently urged in sealing engagement with the valve seat 18. Due to the dome-shaped configuration 33 of the valve element 15, the greater the pressure of the fluid flow in the outlet 12, the greater the sealing force between the neck area 17 and the valve seat 18. The valve 10 may be opened or "cracked" either by fluid pressure in its inlet 11 or by a physical object such as the tip of a syringe that exerts a force on the stem 42 of the valve element 15 against the resilient force inherent in the valve element 15 and as defined by the grooves 19 and 20. As shown in FIGS. 3A and 3B, once the valve element is opened or cracked, fluid flow from the inlet 11 flows around the stem 42 or through notches 38 radially across the outer surface of the dome-shaped configuration 33 of the valve element 15, through the flow channels defined by ribs 41, through the flow channels defined by the castellations 22 and then out via outlet 12. Importantly, a substantial flow of fluid is allowed to pass through the valve once the valve element 15 is cracked. Once the cracking pressure is removed, either by the lack of sufficient pressure of the incoming fluid in inlet 11 or by removal of the object that cracked the valve, the inherent resiliency of the valve element 15 urges the neck 17 back into sealing engagement with the valve seat 18. Significantly, the sealing force caused therebetween is sufficient to assure an adequate seal even when the outlet fluid pressure is very small.

The present disclosure includes that contained in the appended claims, as well as that of the foregoing description. Although this invention has been described in its preferred form with a certain degree of particularity, it is understood that the present disclosure of the preferred form has been made only by way of example and that numerous changes in the details of construction and the combination and arrangement of parts may be resorted to without departing from the spirit and scope of the invention.

Now that the invention has been described,

What is claimed is:

1. A valve, comprising in combination: an inlet housing having a central bore; an outlet housing; an elastomeric valve element having a generally dome-shaped configuration with a central integral stem positioned substantially concentrically therewith, said valve element further including a plurality of notches positioned longitudinally along the length of said stem, said plurality of notches including a larger width toward said inlet and a smaller width toward said dome-shaped configuration and a depth radially inward to define a castellated configuration in said stem; and said inlet housing and said outlet housing being fastened together at a joint with said elastomeric valve element positioned therein with said stem of said valve element extending an appreciable distance into said central bore of said inlet housing such that said stem extending into said central bore aligns said valve element concentrically within said inlet housing while allowing fluid flow through said notches.

2. The valve as set forth in claim 1, wherein said valve element includes a plurality of longitudinal ribs formed along an outer annular periphery of a lower end of said dome-shaped configuration that define flow channels that allow fluid flow from across an upper surface of said dome-shaped configuration through. said flow channels.

3. The valve as set forth in claim 1, wherein said depth of said notches is sufficient to eliminate the need for a stem slot.

4. A valve, comprising in combination: an inlet housing; an outlet housing; an elastomeric valve element having a generally dome-shaped configuration with a central integral stem positioned substantially concentrically therewith, said valve element comprising a plurality of notches positioned longitudinally along the length of said stem and at least one annular relief formed in said dome-shaped configuration to allow easier flexing when said valve element is opened, said relief being positioned in the underside of said dome-shaped configuration; said inlet housing and said outlet housing being fastened together at a joint with said elastomeric valve element positioned therein; and said outlet housing including a plurality of castellations formed along an inner annular periphery of said outlet housing that define flow channels.

5. A valve, comprising in combination: an inlet housing; an outlet housing; an elastomeric valve element having a generally dome-shaped configuration with a central integral stem positioned substantially concentrically therewith, said valve element comprising two reliefs positioned concentrically in the underside of said dome-shaped configuration to allow easier flexing when said valve element is opened; said inlet housing and said outlet housing being fastened together at a joint with said elastomeric valve element positioned therein; and said outlet housing including a plurality of castellations formed along an inner annular periphery of said outlet housing that define flow channels.

6. The valve as set forth in claim 5, wherein said relief comprises a continuous groove.

7. The valve of claim 5, wherein the number and dimensions of said reliefs, together with the elastomeric properties of said element, define the cracking pressure necessary to crack or open the valve element.

8. The valve as set forth in claim 5, wherein an upper portion of said dome shaped configuration of said valve element comprises a generally frustro-conical neck.

9. The valve as set forth in claim 5, wherein said inlet housing comprises an annular valve seat in alignment with said frustro-conical neck to form a fluid- tight annular seal therewith by virtue of the resiliency of said element pushing said frustro-conical neck into sealing engagement with said valve seat.

10. A valve, comprising in combination: an inlet housing; an outlet housing; an elastomeric valve element having a generally dome-shaped configuration having a radius with a central integral stem positioned substantially concentrically therewith; said inlet housing and said outlet housing being fastened together at a joint with said elastomeric valve element positioned therein; and said valve element comprising a at least one annular relief formed in said dome-shaped configuration within said radius to allow easier flexing when said valve element is opened, said relief being positioned in the underside of said dome-shaped configuration.

11. A valve, comprising in combination: an inlet housing; an outlet housing; an elastomeric valve element having a generally dome-shaped configuration with a central integral stem positioned substantially concentrically therewith; said inlet housing and said outlet housing being fastened together at a joint with said elastomeric valve element positioned therein; and said valve element comprising two reliefs positioned concentrically in the underside said dome-shaped configuration to allow easier flexing when said valve element is opened.

12. The valve as set forth in claim 11, wherein at least one of said reliefs comprises a continuous groove.

13. The valve as set forth in claim 11, wherein an upper portion of said dome shaped configuration of said valve element comprises a generally frustro-conical neck.

14. The valve as set forth in claim 11, wherein said inlet housing comprises an annular valve seat in alignment with said frustro-conical neck to form a fluid-tight annular seal therewith by virtue of the resiliency of said element pushing said frustro-conical neck into sealing engagement with said valve seat.

* * * * *